United States Patent [19]

Hunter

[11] Patent Number: 4,971,514
[45] Date of Patent: Nov. 20, 1990

[54] STACKING DEVICE FOR PLATE-LIKE OBJECTS, IN PARTICULAR TITER PLATES OR THE LIKE

[75] Inventor: Don F. Hunter, Grödig, Austria

[73] Assignee: Prolic SA, Luxembourg, Luxembourg

[21] Appl. No.: 321,200

[22] Filed: Mar. 8, 1989

[30] Foreign Application Priority Data

Nov. 14, 1988 [EP] European Pat. Off. ........ 88118918.7

[51] Int. Cl.$^5$ .............................................. B65G 57/00
[52] U.S. Cl. ................................ 414/795.3; 414/788.7; 414/933
[58] Field of Search ............... 414/788.7, 795.3, 798.1, 414/797.4, 933

[56] References Cited

U.S. PATENT DOCUMENTS

| 2,940,327 | 6/1960 | Gartner | 414/795.3 |
|---|---|---|---|
| 3,421,638 | 1/1969 | Locke et al. | 414/788.7 |
| 3,443,706 | 5/1969 | Puhm | 444/798.1 |
| 3,701,314 | 10/1972 | Tull | 414/795.3 |
| 4,180,361 | 12/1979 | Longinotti | 414/795.3 |
| 4,765,487 | 8/1988 | Bliss | 414/795.3 |

FOREIGN PATENT DOCUMENTS 1253163  10/1967  Fed. Rep. of Germany ... 414/795.3

Primary Examiner—David H. Brown
Attorney, Agent, or Firm—Wenderoth, Lind & Ponack

[57] ABSTRACT

Disclosed is a stacking device for stacking and unstacking plate-shaped objects such as titer plates. A magazine is provided to hold the titer plates and a support plate is provided beneath the titer plates. A clamping device is provided to hold the bottom-most titer plate or second titer plate from the bottom. The clamping device preferably has two opposing, horizontal clamping beams which are forced by means of springs against the respective titer plate and which can be moved synchronously away from the titer plate by a motor via a linkage. The clamping beams can also be rotated about a vertical axis so as to adapt to titer plates having different shapes.

19 Claims, 7 Drawing Sheets

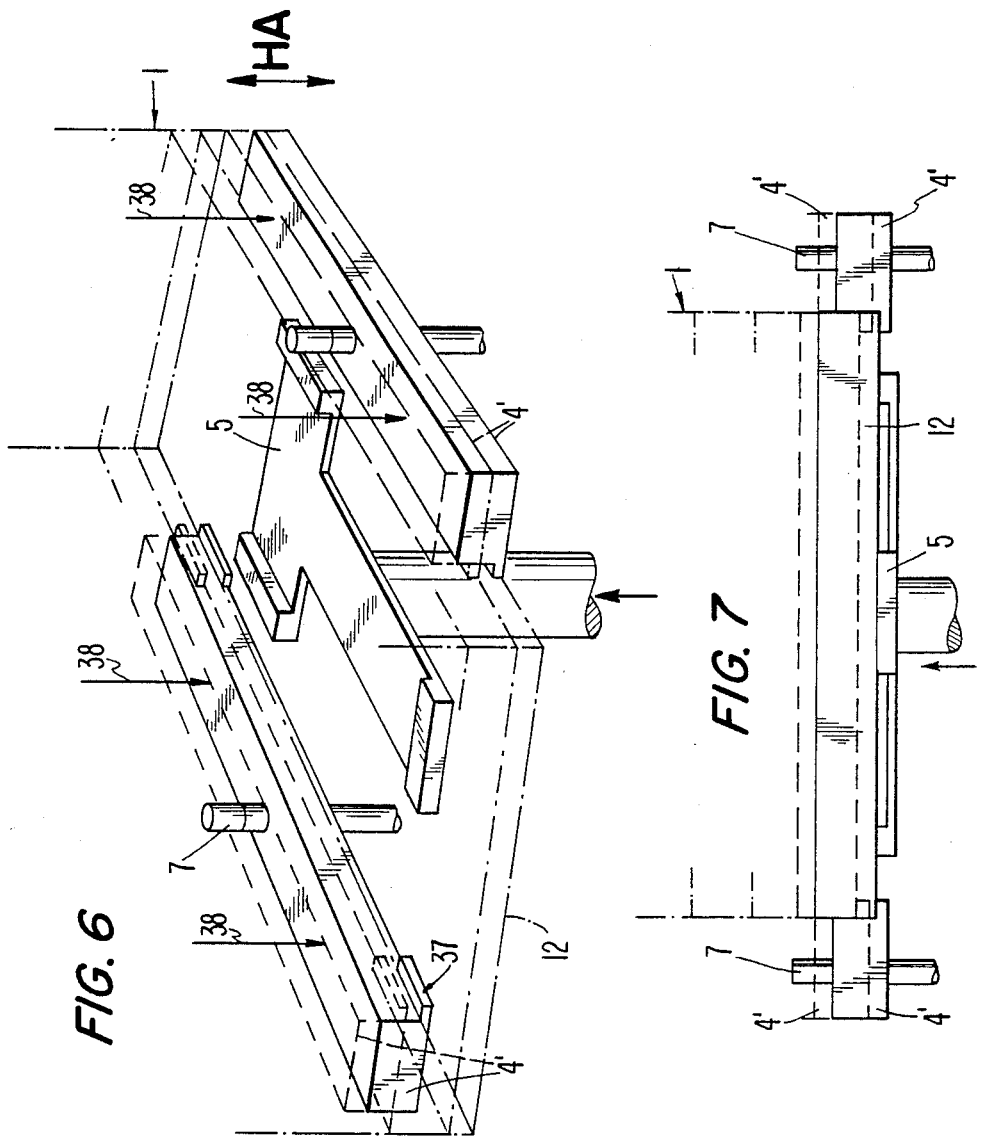

STACKING DEVICE FOR PLATE-LIKE OBJECTS, IN PARTICULAR TITER PLATES OR THE LIKE

FIELD AND BACKGROUND OF THE INVENTION

The invention relates to a stacking device for plate-like objects, and in particular for titer plates or the like, which includes a magazine for holding a stack of the titer plates, a support plate or the like which can be moved between an upper and a lower limit point, a clamping device for clamping the titer plates in the magazine, and at least one spring for biasing the clamping device against the titer plates.

In medical laboratory technology, for example, the Elisa process is used to measure antigens and/or antibodies (enzyme linked immunosorbent assay). For example, in order to measure antigens, antibodies are first absorbed on the titer plate; the titer plate is then washed; and in a subsequent process step, a test liquid containing the antigen is admixed. The next step includes a washing after which enzyme-marked specific antibodies are put on the titer plate. The titer plate is washed again, whereafter a substrate for the enzyme is admixed. Actual measurement of the antigens and/or antibodies is performed in a photometer.

For use of either the photometer or the washing device, it is necessary to have the titer plates unstacked and fed individually thereto.

Once the titer plates leave either the photometer or washing device, it is then necessary for the titer plates to be stacked again.

During the stacking and unstacking process, the fact that the dimensions of titer plates are not completely uniform, that is, that the individual plates may differ in thickness, in width or in the fact that a plate may or may not have an additional lateral edge, has been demonstrated to create a problem with respect to holding the plates.

Prior art stacking devices have attempted to overcome this problem by adjusting the device to the specific dimensions of each titer plate.

SUMMARY OF THE INVENTION

The object of the present invention is to provide a stacking device of the aforementioned kind with which it is possible to stack or unstack different kinds of titer plates without having to make special adjustments for each different titer plate.

This object is achieved by the present invention by providing a stacking device for titer plates which comprises a clamping device having two opposing horizontal clamping beams or members which are adapted to be moved synchronously away from the titer plates by means of a motor and which are arranged so as to be rotatable around vertical axis-defining pins.

Such an arrangement, according to the invention, allows the stack of titer plates to comprise different titer plates. The clamping beams are not forced against the titer plates by the motor but rather by means of springs. This allows the stacking device to accommodate titer plates having varying widths and to always uniformly hold them securely.

Preferably, each clamping beam has two contact projections which contact the titer plates and are, for example, formed by flat ribs or flanges extending inwardly from the clamping beams. These contact projections facilitate the uniform and secure holding of the titer plates, even if the height of the titer plates is not uniform. Each contact projection is provided with a rough coating in order to improve the holding contact between the contact projections and the titer plates. Preferred coating materials for this purpose are tungsten carbide or diamond, since these will provide a hard and disinfectable surface.

In order to prevent the stack of plates from sliding downwardly in case of an accident, inwardly biased pins may be movably mounted to the clamping beams below the position of the contact projections and can be moved relative to the clamping beam so as to extend and be biased inwardly from the clamping beams a distance further than the contact projections. The pins are preferably biased inwardly by extremely weak leaf springs so that when the clamping beams are clamped against the second titer plate from the bottom of the stack, the pins are biased inwardly against the bottom-most titer plate but do not exert a holding force thereagainst. While the spring force is weak, it is sufficient to cause the pins to extend inwardly to engage beneath a downwardly sliding titer plate.

The motor is advantageously connected to the clamping beams via a linkage which provides sufficient play so as to allow the clamping beams to adapt to titer plates having varying widths. This play is possible because the contact between the clamping beams and the titer plates is caused by the springs rather than by the motor. The linkage includes two pairs of racks, each of which includes an outer and an inner rack. Each of the inner racks is connected to the clamping beam on one side of the titer plates and each of the outer racks is connected to the clamping beam on the opposite side of the titer plates. Gear wheels are mounted between the inner and outer racks of each rack pair and positively engage with teeth formed thereon such that when the inner racks are moved in one linear direction, the outer racks are caused to move in the opposite linear direction. The two inner racks are mutually connected by a cross rod which has a pin fixedly mounted thereon. The motor has an eccentric drive pin or shaft which is connected to the pin of the cross rod by a rod having apertures in each end which receive the eccentric drive pin and the cross rod pin, respectively.

The play provided by the linkage can be provided by making each of the apertures at the ends of the rod, which connects the motor to the cross rod, sufficiently large to loosely encircle the respective pin which the aperture receives. Alternatively, the aperture which receives the eccentric drive pin can be of a size which causes it to rotatably but closely encircle the pin, and the aperture at the other end of the rod can be foremd as a longitudinal slot so as to slidably encircle the pin. The longitudinal slot is formed in such a manner that the perimeter of the longitudinal slot forms a stop which prevents any one of the titer plates from being clamped too tightly by the clamping beams.

The invention may also provide for the clamping beams to be moved vertically from a bottom position of rest to a top position in which the titer plates held by the clamping beams are barely below an upper limit point of the support provided by a magazine which holds the stack of titer plates. This is an advantageous feature because it allows the titer plates to be stacked, unstacked and transferred with absolutely no vibrations induced in the titer plates by the support plate. Without such a feature, the support plate may jolt the titer plates when moved upwardly to support them due to lack of precision in positioning the support plate. Similarly, if the lack of precision causes the support plate to be positioned slightly below the bottom of the bottom-most titer plate, the titer plates will be jolted when released from the clamping beams because they will fall onto the support plate. The vertical adjustability of the clamping beams nullifies this problem such that vibrations are not induced in the titer plates. It is also contemplated that the clamping beams may be biased downwardly by a spring into their bottom rest position.

Another embodiment of the invention provides that the clamping beams have preferably rib-like projections extending inwardly toward the titer plates from bottom edges of the clamping beams so as to extend beneath the titer plate which is being held by the clamping beams. These rib-like projections, like the inwardly biased pins, will prevent a sliding titer plate from falling through the clamping beams. These projections are shaped so as to allow the titer plates to be restacked.

It is also contemplated that the invention may include a hangar-shaped carrier used for feeding a titer plate from one magazine to another. Preferably, the carrier has a center rib disposed parallel to one side of the titer plate and two slanted carrier ribs extending therefrom at like angles in a diverging manner such that they are adapted to contact front and rear corners of the titer plate. The carrier is thus arranged to position the titer plate such that it is always exactly centered in the desired position by the diverging carrier ribs. Thus, when positioned in a work area or below a stack of titer plates to which the titer plate is to be guided, the titer plate is always properly oriented for the purpose. When two stacking devices according to the present invention are used with an analysis device, the titer plates can be readily stacked, unstacked and restacked such that they are maintained in the same sequence and can be guided to a subsequent testing station without the need for an intermediate station.

Note that the stacking device of the present invention is not limited to use with titer plates but can also be advantageously utilized for handling other types of plate-shaped objects or stackable members.

BRIEF DESCRIPTION OF THE DRAWING FIGURES

The invention will now be described with reference to the drawing figures, in which:

FIG. 6 is a perspective view of alternative clamping beams according to the invention;

FIG. 7 is a side view of the embodiment of FIG. 6;

DETAILED DESCRIPTION OF THE INVENTION

Figure 1:
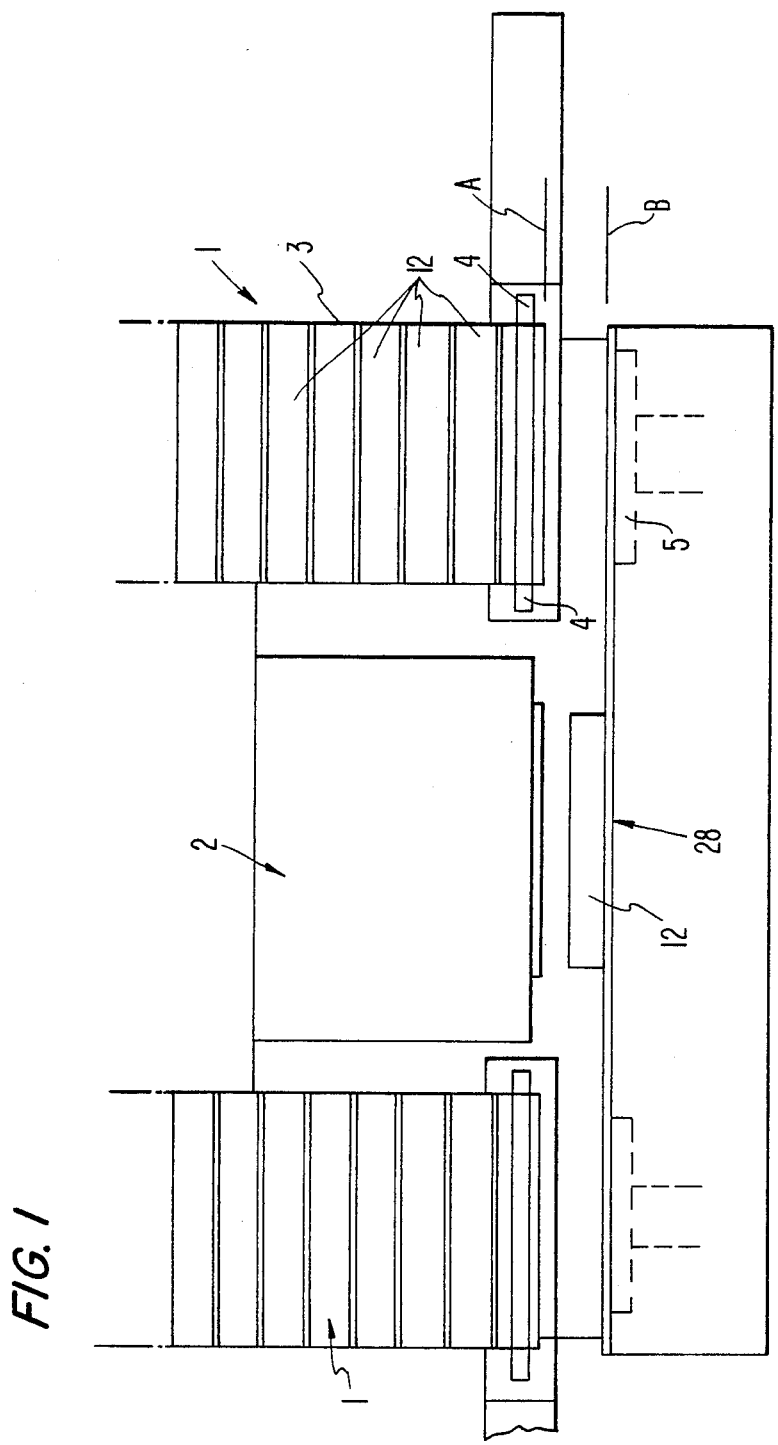
FIG. 1 is a schematic side view of an analysis device utilizing two stacking devices according to the invention.

As shown in FIG. 1, a stacking device 1 of the invention can be arranged along a processing line longitudinally before and after a photometer 2. The main components of the stacking device of the invention are a magazine 3, two elongated clamping members or beams 4, and a support plate 5.

The support plate 5 which supports a stack of titer plates from below is, for example, movable vertically by means of a piston/cylinder unit 6 so that the respective bottom-most titer plate is lowered from position A in the magazine 3 to a level B (see FIG. 1). The support plate 5 is preferably formed such that the titer plates will be contacted from below by three remote points of the support plate and thus be supported in a stable manner.

Figure 5:
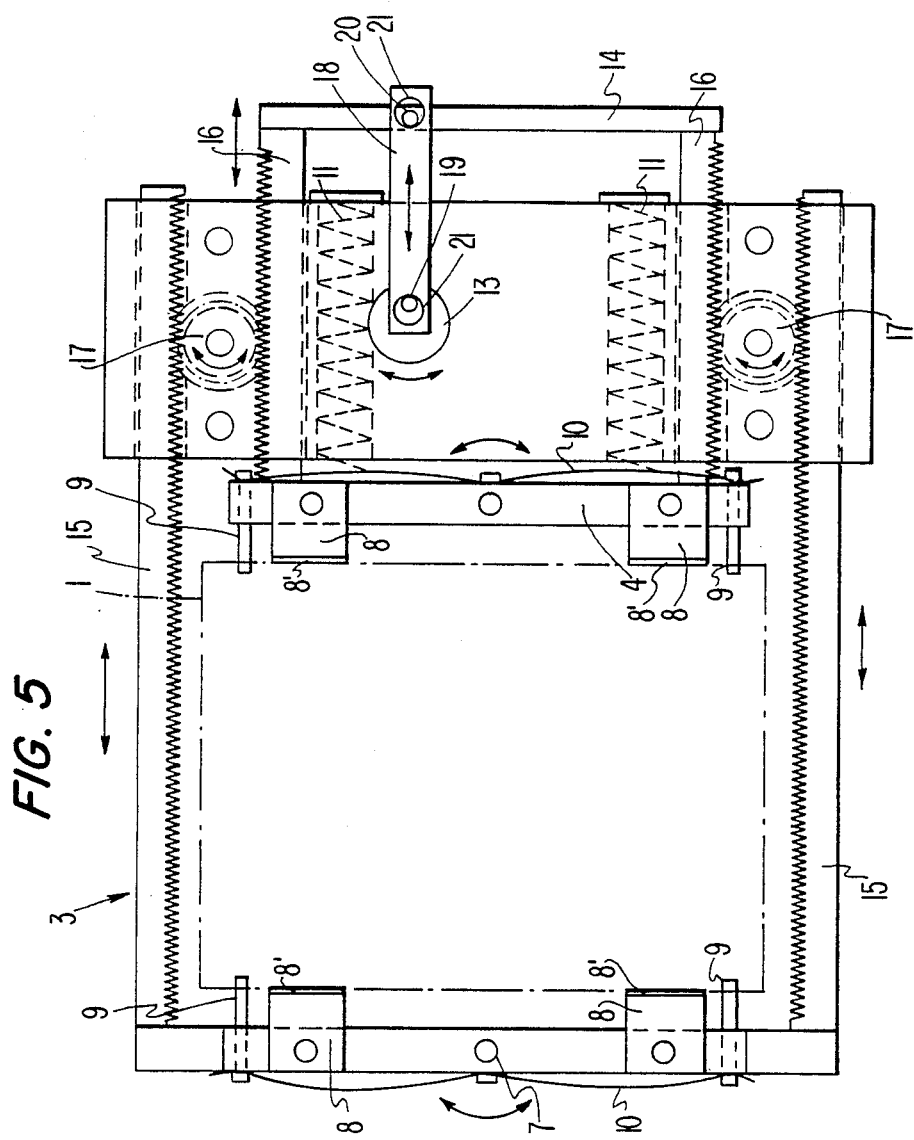
FIG. 5 is a schematic top view of the stacking device of the invention.

The clamping beams 4 are arranged on either longitudinal side of the magazine 3. The clamping beams 4 are mounted on pins 7 for rotation in the directions of the arrows shown in FIG. 5 about axes extending longitudinally through the centers of the pins 7. This ability to rotate allows the clamping beams 4 to be repositioned to compensate for irregularities on the edges of the titer plate 12.

Flanges 8 extend inwardly from an upper portion of each end of each clamping beam 4 and act to clampingly contact the titer plates 12. Pins 9 extend through each end of each beam 4 and are biased inwardly toward the titer plates by relatively weak leaf springs 10 and are adapted to extend beneath a downwardly sliding titer plate to prevent it from falling through the clamping beams. The flanges 8 are preferably coated with a coating material 8' such as, for example, tungsten carbide or diamond so as to improve the holding contact between flanges 8 and the titer plates. The clamping beams 4 on one side of the titer plates 12 are biased toward the plates 12, by two pressure springs to thereby provide a clamping force against the titer plates 12.

The titer plate 12 can be selectively released from their clamped condition by a motor 13 which is connected to the clamping beams 4 by a linkage. The linkage includes two pairs of racks, each of which includes an outer rack 15 and an inner rack 16. Each of the inner racks 16 is connected to the clamping beam 4 on one side of the magazine 3 and each of the outer racks 15 is connected to the clamping beam 4 on the opposite side of the magazine 3. The inner and outer racks of each rack pair have gear teeth formed thereon on mutually facing surfaces. A gear wheel 17 is mounted about a fixed axis between the inner and outer rack and is positively engaged with the teeth of each rack. A cross rod 14 spans between and connects distal ends of each of the inner racks 16. The motor 13 includes an eccentrically driven pin or shaft 19 and an anchoring pin is fixed to the cross rod 14. A rod 18 which includes large holes 21 formed in end portions thereof connects between the eccentric pin 19 and the anchoring pin 20, such that when motor 13 causes eccentric motion of pin 19, the inner racks 16 are moved linearly toward or away from the magazine 3. The linear movement of the inner racks causes rotation of gear wheels 17 which, in turn causes linear motion of the outer racks 15 in a direction opposite to the direction of the inner racks 16.

The connections between the rod 18 and the motor 13 and cross rod 14, respectively, are formed by the large holes 21 loosely encircling the pins 19 and 20, respectively. Having the holes 21 loosely encircle the pins 19 and 20 does not result in there being play between the clamping beams 4 and the titer plates 12 because springs 11 maintain the clamping beams 4 in clamping relation to the titer plates 12. The loose connections between the holes 21 nd the pins 19 and 20 do, however, allow the clamping beams 4 to adapt to titer plates of slightly varying widths because it provides the racks 15 and 16 with sufficient play to allow the clamping beams 4 to rotate slightly about pins 7.

Figure 2:
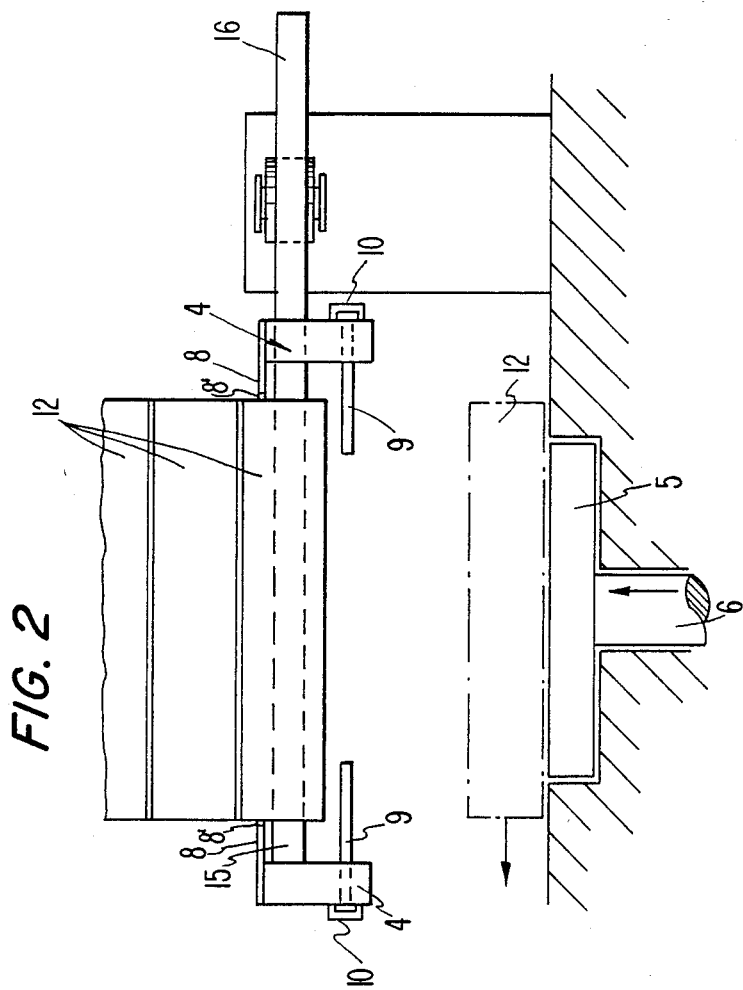
FIGS. 2, 3 and 4 are schematic side views of the stacking device of the invention, illustrating the stages of stacking or unstacking a titer plate therefrom.
Figure 4:
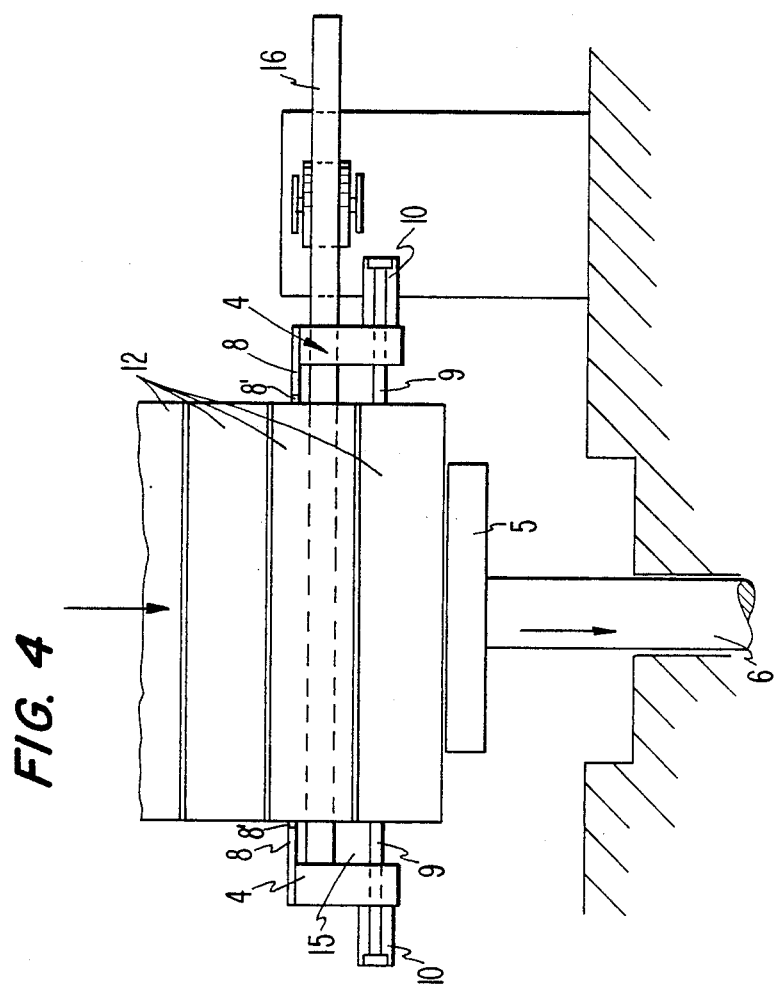

By using the stacking device of the present invention the titer plates 12 can be unstacked in the following manner. While the stack of titer plates 12 is being supported from below by the support plate 5 at such a height that the second titer plate from the bottom of the stack is aligned with the clamping beams 4, the two clamping beams 4 are caused to clamp against the second titer plate from the bottom by means of motor 13, linkage 14–21, and springs 11 (see FIG. 4). The support plate 5 is then lowered to the level B (see FIGS. 1 and 2) by the piston cylinder unit 6, carrying with it the bottom most titer plate. The titer plate thus carried to level B can be further transported horizontally by conventional means of conveyance (not shown).

Figure 3:
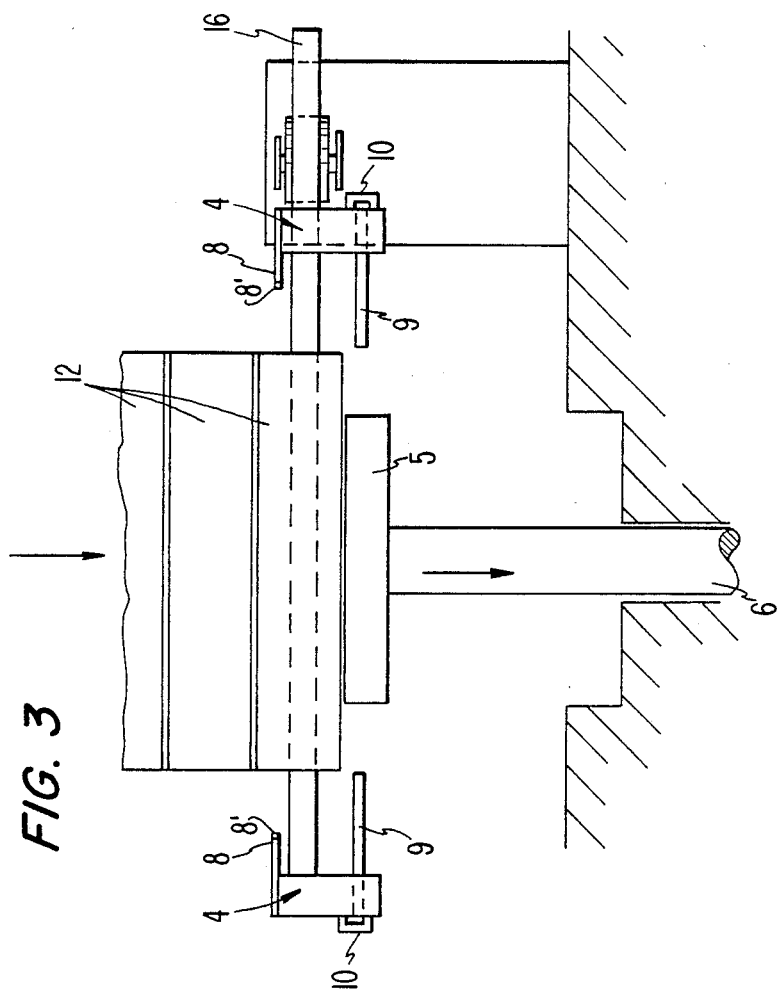

The thus emptied support plate 5 is then returned to its upper position wherein it supports the stack of titer plates 12 from below. Next, the stacking device of the present invention is readied (see FIG. 3) to unload additional titer plates by energizing the motor to cause the clamping beams 4 to move laterally away from and thus unclamp the bottom-most titer plate 12 against inward bias of the springs 11. The support plate 5 is then moved downwardly a distance equal to the height of one titer plate 12 so as to vertically align the second titer plate from the bottom of the stack with the clamping beams 4. The motor 13 can then be energized so as to cause the clamping beams 4 to again be biased against and in clamping relation to the second titer plate from the bottom of the stack to thus secure the entire stack of titer plates 12 (see FIG. 4). The process can be repeated as often as desired in order to unstack additional titer plates.

The above process can, of course, be performed in reverse in order to stack the titer plates. That is, from the state in which the clamping beams 4 are clamped against the second titer plate from the bottom of the stack, the clamping beams are first moved outwardly to unclamp the titer plates, the support plate 5 is moved upwardly a distance equal to the height of one titer plate, the clamping beams are clamped against the bottom most titer plate to thereby support the stack of titer plates 12, and the support plate is lowered to level B so as to be in position to receive an additional titer plate thereon. A titer plate is then moved onto the support plate by conventional means and the support plate is raised until the new titer plate comes in contact with the stack of titer plates. This process can be repeated as often as desired in order to stack additional titer plates.

FIGS. 6 and 7 show an alternative type of clamping beam 4' which can be used in the present invention. These clamping beams 4' have two narrow rib-like projections 37 which extend laterally inwardly and are adapted to extend under one of the titer plates when the titer plate is clamped by the clamping beams 4' so that the projections 37, like the pins 9 of the embodiment of FIG. 1–5, will prevent a sliding titer plate 12 from falling through the clamping beams 4'.

FIGS. 6 and 7 show that the clamping beams 4' can be moved vertically in the direction of the double arrow HA so that the height of the stack of titer plates can be adjusted by merely moving the clamping beams 4'. This vertical adjustment is advantageous because it is often difficult to vertically position the support plate 5 precisely relative to the bottom-most titer plate. This lack of precision can cause the support plate 5, when moved upwardly, to hit and thus vibrate the titer plates 12 or can cause the support plate to be positioned slightly below the bottom-most titer plate such that when the clamping beams 4' are released from the titer plates, the titer plates drop onto the support plate 5 and are thus vibrated by the contact. It is also contemplated that the clamping beams can be biased downwardly by springs (schematically illustrated in FIG. 6 by arrows 38).

This vertical adjustment is important for use during both stacking and unstacking to reduce vibrations imparted to the titer plates 12.

Figure 8:
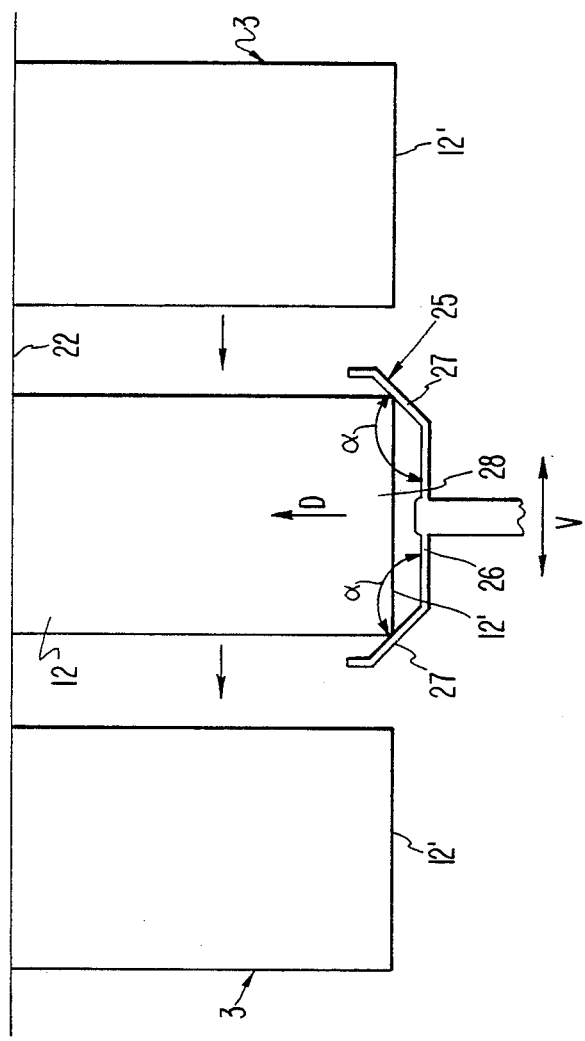
FIG. 8 is a schematic top view of a horizontal feeder according to the invention.

FIG. 8 shows a hangar-shaped carrier 25 for use in the stacking device of the present invention. This carrier 25 is used to feed a titer plate 12 from a first magazine 3 to a second magazine 3 via a work area 28.

Figure 9:
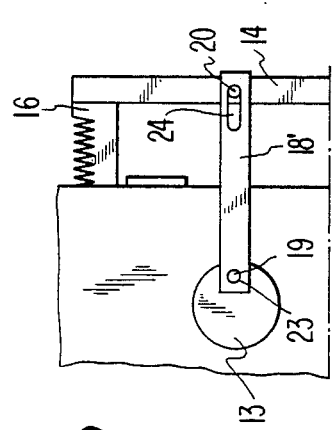
FIG. 9 is a top view of an alternative drive linkage for the clamping beams according to the invention.

The carrier 25 can be moved in the direction of the double arrow V. It includes a rib 26 disposed parallel to the longitudinal side 12' of the titer plate 12 and two laterally diverging carrier ribs 27, each of which extends from the rib 26 at a like angle a. Each of the carrier ribs 27 presses against a corner of the titer plate 12 such that, when the carrier 25 forces the titer plate 12 in the direction of the arrow D, against an opposing surface 22, the titer plate 12 is automatically centered in the carrier 25, and is thus properly oriented in the working area 28 situated beneath the magazines 3. FIG. 9 illustrates a rod 18' which is a modified form of the rod 18 shown in FIG. 5, which connects the motor 13 to the cross rod 14. Rather than providing large holes at each end of the rod to loosely encircle the pins 19 and 20, a hole 23 is provided at one end which tightly, but rotatably, receives pins 19 therein and a longitudinal slot 24 is provided at the other end which rotatably slidably receives anchoring pin 20. The length of the slot 24 is such that the perimeter of the slot 24 acts as a stop so that no titer plate 12 can be clamped too tightly.

Although the stacking device of the present invention has been described particularly for use with titer plates, it is to be noted that the stacking device is equally operable for use with other plate-shaped objects and stackable members.

What is claimed is:

1. A device for stacking and unstacking objects, comprising:
   support means for supporting the objects from below and for selectively moving the objects vertically;
   clamping means, for selectively clamping against at least one of the objects, comprising first and second opposing elongated clamping members each of which is rotatably mounted about an axis-defining pin, and means for driving said clamping members toward or away from one another so as to cause said clamping members to move toward or away from the at least one of the objects; and
   means for biasing said first and second clamping members toward one another, said biasing means comprising two compression springs mounted to said driving means and acting against one of said first and second clamping members on respectively opposite sides of its respective axis-defining pin.

2. A device as recited in claim 1, wherein said elongated clamping members are mounted substantially horizontally.

3. A device as recited in claim 1, further comprising means for urging said clamping members downwardly.

4. A device as recited in claim 1, further comprising a carrier means for feeding the objects horizontally along a path between first and second stacks, said carrier means comprising a center rib mounted substantially parallel with said path between said first and second stacks, and two carrier ribs connected to and extending away from said center rib at like angles thereto, said carrier ribs being adapted to abut against corners of the objects as the objects are being fed along said path.

5. A device as recited in claim 1, wherein said clamping means further comprises at least one substantially horizontal pin horizontally movably mounted respectively to each of said first and second clamping members and extending inwardly toward the other of said first and second clamping members.

6. A device recited in claim 5, wherein said at least one pin comprises two pins.

7. A device as recited in claim 5, wherein said extending means comprises means for pressing each of said pins inwardly relative to said first and second clamping members, respectively.

8. A device as recited in claim 7, wherein said pressing means comprises a weak leaf spring mounted to each of said clamping members.

9. A device as recited in claim 1, wherein said driving means comprises a motor and a linkage operatively connecting said motor to said clamping members;
said linkage comprises means for drivingly connecting said motor to said clamping members such that, upon activation of said motor, said first clamping member is moved in one direction and said second clamping member is moved in a direction opposite said one direction; and
said means for drivingly connecting comprises a first rack member connected to said first clamping member and having teeth, a second rack member connected to said second clamping member and having teeth facing toward said teeth of said first rack member, and a gear wheel rotatably mounted about a fixed axis between and in positive engagement with said first and second rack members.

10. A device as recited in claim 9, wherein said means for drivingly connecting further comprises a third rack member connected to said first clamping member and having teeth, a fourth rack member connected to said second clamping member and having teeth facing toward said teeth of said third rack member, and a second gear wheel rotatably mounted about a fixed axis between and in positive engagement with said third and fourth rack members.

11. A device as recited in claim 9, wherein said first rack member has first and second ends, said first end is connected to said first clamping member, said motor has an eccentric output shaft, and said means for drivingly connecting further comprises a cross rod connected to said second end of said first rack, an anchoring pin mounted to said cross rod, and a rod having first and second apertures through respectively opposite ends thereof receiving said eccentric output shaft and said anchoring pin, respectively.

12. A device as recited in claim 11, wherein said first and second apertures loosely encircle said eccentric output shaft and said anchoring pin, respectively.

13. A device as recited in claim 11, wherein said first aperture rotatably and tightly receives said eccentric output shaft, and said second aperture comprises a slot which rotatably and slidably receives said anchoring pin.

14. A device as recited in claim 1, wherein each clamping member includes at least two contact projections extending inwardly therefrom toward the other of said first and second clamping members and adapted to contact the at least one of the objects, each of said contact projections comprising a substantially horizontal flat flange with a rough coating thereon, and including a distal end which is adapted to contact the at least one of the objects.

15. A device as recited in claim 14, wherein said rough coating comprises tungsten carbide.

16. A device as recited in claim 14, wherein said clamping means further comprises at least one substantially horizontal pin horizontally moveably mounted respectively to each of said first and second clamping members at locations below where said contact projections are mounted and extending inwardly toward the other of said first and second clamping members, and means for extending each of said pins inwardly further than said contact projections extend.

17. A device recited in claim 16, wherein said at least one pin comprises two pins.

18. A device as recited in claim 16, wherein said extending means comprises means for pressing each of said pins inwardly relative to said first and second clamping members, respectively.

19. A device as recited in claim 18, wherein said pressing means comprises a weak leaf spring mounted to each of said clamping members.

* * * * *